United States Patent [19]

Davies et al.

[11] Patent Number: 5,039,686
[45] Date of Patent: Aug. 13, 1991

[54] N-PYRIDYL NITROMETHYLENE HETEROCYCLIC COMPOUNDS AND THEIR USE AS PESTICIDES

[75] Inventors: John H. Davies, Canterbury; Michael Pearson, Teynham; Arthur C. Wilson, Bearsted, all of England

[73] Assignee: Shell Internationale Research Maatschappij B.V., Netherlands

[21] Appl. No.: 429,806

[22] Filed: Oct. 31, 1989

[30] Foreign Application Priority Data

Nov. 14, 1988 [GB] United Kingdom ............ 8826539.2

[51] Int. Cl.$^5$ ................ C07D 401/04; A61K 31/435
[52] U.S. Cl. ................... 514/341; 514/256; 514/218; 546/278; 544/333; 540/553
[58] Field of Search ............ 546/278; 544/333; 540/553; 514/341, 256, 218

[56] References Cited

U.S. PATENT DOCUMENTS 4,647,570  3/1987  Shiokawa et al. ............ 514/341

Primary Examiner—Jane T. Fan

[57] ABSTRACT

The invention provides nitromethylene compounds of general formula

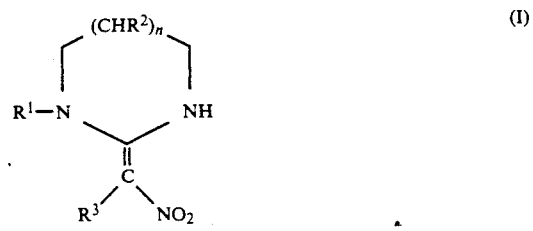

wherein n is 2, 3, or 4, $R^1$ is an optionally substituted 3-pyridyl group, each $R^2$ is independently selected from an alkyl group, a haloalkyl group or a hydrogen atom, and $R^3$ is a hydrogen atom or an alkylcarbonyl group, processes for their preparation, and their use as pesticides, particularly insecticides.

7 Claims, No Drawings

N-PYRIDYL NITROMETHYLENE HETEROCYCLIC COMPOUNDS AND THEIR USE AS PESTICIDES

This invention relates to nitromethylene compounds, particularly nitromethylene heterocyclic compounds, to processes for their preparation, and to the use of such compounds as pesticides.

W. German Offenlegungsschrift 2514402 (DE-A-2514402) discloses 2-nitromethylene compounds of formula

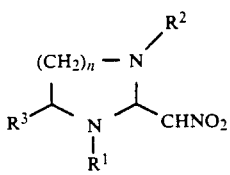

in which n is 1 or 2, $R^1$ is hydrogen, a straight- or branched-chain alkyl group of not more than 8 carbon atoms, $C_{5-6}$cycloalkyl, $C_{2-4}$hydroxyalkyl, alkoxyalkyl of up to 8 carbon atoms, N,N-dialkylaminoalkyl of up to 7 carbon atoms, phenyl or phenyl-$C_{1-2}$alkyl, and $R^2$ and $R^3$ are hydrogen or methyl. These compounds are disclosed as of use as insecticides. Also disclosed is their synthesis by reacting a compound of formula

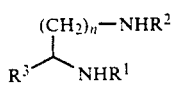

wherein $R^1$, $R^2$, $R^3$ and n are defined above, with a compound of formula

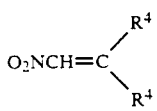

wherein $R^4$ is $C_{1-4}$alkylthio or halogen, especially chlorine.

It has now been found that a certain novel class of nitromethylene compounds exhibits surprisingly effective pesticidal, particularly insecticidal, activity.

According to the present invention there are provided nitromethylene compounds of general formula

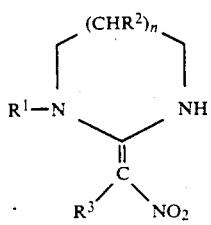
(I)

wherein n is 2, 3 or 4;
$R^1$ is an optionally substituted 3-pyridyl group; each $R^2$ is independently selected from an alkyl group, a haloalkyl group or a hydrogen atom; and
$R^3$ is a hydrogen atom or an alkylcarbonyl group.
Preferably n is 2 or 3.

Examples of optional substituents on a 3-pyridyl group include halogen atoms and alkyl, alkoxy, alkylthio, haloalkyl, cyano, alkoxycarbonyl, alkylamino, dialkylamino, (alkylcarbonyl)alkylamino, (alkoxycarbonyl)alkylamino, alkylcarbonylamino, and alkoxycarbonylamino groups. Any alkyl moiety in such substituents is preferably $C_{1-6}$alkyl, more preferably $C_{1-4}$alkyl.

$R^1$ is preferably a 3-pyridyl group substituted in the 6-position by a halogen atom, a $C_{1-4}$alkoxy group, a $C_{1-4}$alkylthio group, a $C_{1-4}$haloalkyl group, a cyano group or a ($C_{1-4}$alkoxy)carbonyl group, more preferably a 3-pyridyl group substituted in the 6-position by a chlorine or bromine atom, a methoxy group, a di- or trifluoromethyl group, or a cyano group. Advantageously, $R^1$ is a 6-chloro-3-pyridyl group or a 6-bromo-3-pyridyl group.

Alkyl moieties present in groups represented by $R^2$ are preferably $C_{1-6}$ alkyl, more preferably $C_{1-4}$ alkyl, with methyl and ethyl being especially preferred. Whilst any of the moieties represented by $R^2$ in the —$(CHR^2)_n$— group in compounds of formula I in which n is 3 or 4 may be alkyl or haloalkyl, it is preferred that alkyl or haloalkyl moieties represent by $R^2$ in such compounds are attached to carbon atoms having an adjacent nitrogen atom. Each $R^2$ is preferably a hydrogen atom.

Alkyl moieties present in groups represented by $R^3$ are preferably $C_{1-6}$ alkyl, more preferably $C_{1-4}$ alkyl, with methyl and ethyl being especially preferred. $R^3$ preferably represents a hydrogen atom.

Those skilled in the art will appreciate the possibility of the compounds of formula I existing as isomers (cis- and trans-isomers) and as tautomers. All such isomers and tautomers and their mixtures are embraced by the present invention.

The invention further provides a process for the preparation of a compound of general formula I as defined above which comprises reacting a compound of formula $$R^1-NH-(CHR^2)_n-NH_2 \qquad (II)$$

wherein $R^1$, $R^2$ and n are as defined above, with a nitroethene compound of formula

wherein X represents a $C_{1-4}$alkylthio group or a halogen atom, to yield a compound of general formula I in which $R^3$ is a hydrogen atom, optionally followed by converting the compound so obtained into a compound of general formula I in which $R^3$ is an alkylcarbonyl group.

When X represents a halogen atom, it is preferably a chlorine atom. X is advantageously a methylthio group.

Reaction of the compound of formula II with the compound of formula III may conveniently be effected in the presence of an inert solvent such as alcohols, conveniently ethanol, or other polar solvents such as dimethylformamide, dimethylacetamide, N-methylpyrrolidone, dimethylsulphoxide or acetonitrile. The reaction may conveniently be effected at a temperature in the range 25° C. to the reflux temperature of the reaction mixture, very conveniently at the reflux temperature.

Conversion of the compound of general formula I in which $R^3$ is a hydrogen atom to a compound of general formula I in which $R^7$ is an alkylcarbonyl group may be effected by reaction with an anhydride of formula

wherein $R^4$ is the alkyl moiety required to be present in the alkylcarbonyl group represented by $R^3$ in the compound of formula I. The reaction may conveniently be effected without solvent. Alternatively, the reaction may be effected in the presence of an inert solvent such as an alcohol, conveniently ethanol. The reaction may conveniently be effected at a temperature in the range of from 25° C. to the reflux temperature of the reaction mixture.

Anhydrides of formula IV are known compounds, or may be prepared in analogous methods to those for preparing known anhydrides. For example, acetic anhydride and propionic anhydride are commercially available, e.g. ex Aldrich Chemie N.V., Brussels, Belgium.

The compounds of formula III are known and are described in DE-A-2514402. 1,1-bismethylthio-2-nitroethene is specifically described by Gompper and Schaeffer, Chem. Ber., 100, 591–604 (1967).

The compounds of formula II may be prepared by reacting an aminoalkylphthalide of formula

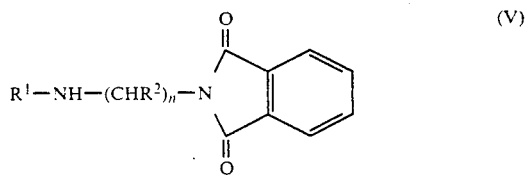

wherein $R^1$, $R^2$ and n are as defined above with hydrazine, followed by treatment with an acid, conveniently hydrochloric acid. Reaction with hydrazine may conveniently be effected in alcoholic medium, e.g. methanol, conveniently at reflux temperature.

The compounds of formula V may be prepared by reacting an optionally substituted 3-aminopyridine with an N-(haloalkyl)phthalimide of formula

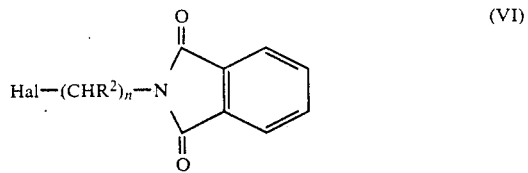

wherein $R^2$ and n are as defined above and Hal is a halogen atom, preferably bromine. Reaction may be effected without solvent, and conveniently at a temperature in the range 100° to 130° C., e.g. about 120° C.

Optionally substituted 3-aminopyridines are known materials, or may be prepared in analogous methods to those for preparing known 3-aminopyridines. For example 5-amino-2-chloropyridine (3-amino-6-chloropyridine), and 5-amino-2-methoxypyridine (3-amino-6-methoxypyridine) are commercially available, e.g. ex Aldrich Chemie N.V., Brussels, Belgium.

N-(haloalkyl)phthalimides of formula VI are known materials or may be prepared in analogous methods to those for preparing known N-(haloalkyl) phthalimides. For example N-(3-bromopropyl)phthalimide, N-(2-bromoethyl)phthalimide and N-(4-bromobutyl)phthalimide are commercially available, e.g. ex Aldrich Chemie N.V., Brussels, Belgium.

The compounds of general formula I exhibit pesticidal, particularly insecticidal, activity. Accordingly the invention also provides a pesticidal composition comprising a carrier and, as active ingredient, a compound of general formula I. The invention further provides a method of combating pests at a locus, which comprises treating the locus with a pesticidal compound or composition according to the invention, and specifically provides the use as an insecticide of a compound of general formula I.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montomorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilizers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilizers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilizers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

Compositions in accordance with the invention may also contain other ingredients, for example other compounds possessing pesticidal, herbicidal, or fungicidal properties. The compounds of the invention may be found to be especially useful when applied in admixture with other insecticides and/or acaricides, e.g. organophosphates, pyrethroids, ureas and organotin compounds, for example the commercial products fenvalerate, permethrin, cypermethrin, deltamethrin, alphacypermethrin, fenbutatin oxide, flufenoxuron, diflubenzuron and trefluron.

The invention will be further understood from the following illustrative Examples, in which Examples 1 to 6 relate to the preparation of starting materials, Examples 7 to 16 relate to compounds of the invention and their preparation and Example 17 relates to pesticidal activity tests.

EXAMPLE 1

Preparation of N-(N-(6

-chloro-3

-pyridyl)-3

-aminopropyl]phthalimide

2-Chloro-5-aminopyridine (28 g, 0.218 mol) and N-(3-bromopropyl)phthalimide (58.4 g, 0.218 mol) were stirred together at ambient temperature (20° C.). The resulting mixture was heated to 120° C. and held at that temperature for 30 minutes whilst vigorous stirring was maintained. The mixture was allowed to cool, and when the temperature had reduced to 60° C., methanol (500 ml) was added and stirring was maintained until a homogeneous solution was obtained. The solution was then cooled to ambient temperature (20° C.), silica gel, 230 to 400 US mesh (0.062 mm to 0.037 mm) (100 g) was added and the mixture was evaporated to dryness. The title product was isolated from the dried mixture by flash chromatography on a silica column using silica gel, 230 to 400 US mesh (0.062 mm to 0.037 mm), and with 2.5% w methanol in dichloromethane as eluent. The resulting product was recrystallized from ethanol to give N-(N-(6-chloro-3-pyridyl)-3-aminopropyl)phthalimide as a buff solid (12 g, 35%) m.p. 140° C.

EXAMPLE 2

Preparation of N-(6

-chloro-3

-pyridyl)-1,3

-diaminopropane

The product of Example 1 (10.5 g, 0.033 mol) was dissolved in methanol (150 ml) and hydrazine hydrate (1.67 g, 0.033 mol) was added. The resulting solution was heated under reflux for 5 hours. The mixture was then cooled to ambient temperature (20° C.), a mixture of concentrated hydrochloric acid (100 ml) and water (100 ml) was added directly, and the resulting mixture was heated under reflux for 5 hours, before being cooled, diluted with water (100 ml) and rendered basic by addition of solid potassium hydroxide whilst cooling (ice/acetone bath). The resulting basic mixture was extracted with chloroform (2×200 ml). The combined chloroform extracts were evaporated to give N-(6-chloro-3-pyridyl)-1,3-diaminopropane (6.0 g, 97%) as a brown oil. NMR (CDCl$_3$), delta: 1.55 (broad s, 1H), 1.65 (quintet, 2H), 2.76 (t, 2H), 3.08 (t, 2H), 4.65 (broad s, 1H), 6.76 (d/d, 1H), 6.98 (d, 1H), 7.65 (d, 1H).

EXAMPLE 3

Preparation of N-(N-(6

-chloro-3

-pyridyl)-2

-aminoethyl)phthalimide

2-Chloro-5-aminopyridine (12.85 g, 0.1 mol) and N-(2-bromoethyl)phthalimide (25.4 g, 0.1 mol) were stirred together at ambient temperature (20° C.). The resulting mixture was heated to 120° C. and held at that temperature for 30 minutes whilst vigorous stirring was maintained. The mixture was allowed to cool, and when the temperature had reduced to 60° C., methanol (250 ml) was added and stirring was maintained until a homogeneous solution was obtained. The solution was then cooled to ambient temperature (20° C.), silica gel, 230 to 400 US mesh (0.062 mm to 0.037 mm) (50 g) was added and the mixture was evaporated to dryness. The title product, (N-(N-(6-chloro-3-pyridyl)-2-aminoethyl)phthalimide, was isolated from the dried mixture by flash chromatography on a silica column using silica gel, 230 to 400 US mesh (0.062 mm to 0.037 mm), and with 2% w methanol in dichloromethane as eluent, as a buff solid (7 g, 46%).

NMR (CDCl$_3$), delta: 3.4 (t, 2H), 4.98 (t, 2H), 4.2 (broad s, 1H), 6.9 (d/d, 1H), 7.05 (d, 1H), 7.73 (m, 3H), 7.85 (m, 2H).

EXAMPLE 4

Preparation of N-(6-chloro-3-pyridyl)-1,2-diaminoethane

The product of Example 3 (1.33 g, 0.0044 mol) was dissolved in methanol (100 ml) and hydrazine hydrate (0.22 g, 0.0044 mol) was added. The resulting solution was heated under reflux for 5 hours. The mixture was then cooled to ambient temperature (20° C.), a mixture of concentrated hydrochloric acid (50 ml) and water (50 ml) was added directly, and the resulting mixture was heated under reflux for 5 hours, before being cooled, diluted with water (50 ml) and rendered basic by addition of solid potassium hydroxide whilst cooling (ice-/acetone bath). The resulting basic mixture was extracted with chloroform (2×100 ml). The combined chloroform extracts were evaporated to give N-(6-chloro-3-pyridyl)-1,2-diaminoethane (0.7 g, 93%) as a brown oil.

NMR (CDCl$_3$), delta: 1.4 (broad s, 1H), 2.85 (t, 2H), 3.05 (t, 2H), 4.5 (broad s, 1H), 6.8 (d/d, 1H), 6.98 (d, 1H), 7.65 (d, 1H).

EXAMPLE 5

Preparation of N-(N-(6-chloro-3-pyridyl)-3-aminobutyl)phthalimide a) 1,3 dibromobutane (10.8 g, 0.05 mol) and potassium phthalimide (9.25 g, 0.05 mol) were added to dry N,N dimethylformamide (100 ml) and the resulting mixture stirred at ambient temperature (20° C.) overnight. The resulting mixture was filtered to remove any solid and the solvent removed from the filtrate to give a colourless oil. The product, N-(3-bromobutyl)phthalimide, was isolated from the oil by flash chromatography on a silica gel column using silica gel, 230 to 400 US mesh (0.062 mm to 0.037 mm) eluted with 2% methanol in dichloromethane as a brown solid in a yield of 7.9 g (55.7%).

NMR (CDCl$_3$), delta: 1.75 (d,3H), 2.18 (q, 2H), 3.85 (m, 2H), 4.1 (m, 1H), 7.7 (m, 2H), 7.85 (m, 2H).

b) The product of a) above (5.3 g, 0.019 mol) and 2-chloro-5-amino pyridine (4.82 g, 0.037 mol) were stirred together and the resulting mixture heated to between 50° to 60° C. and held in this temperature range for 1.5 hours. The resulting mixture was dissolved in methanol (100 ml) with stirring until a homogeneous solution was obtained. The resulting solution was cooled to ambient temperature (20° C.), silica gel, 230 to 400 US mesh (0.062 mm to 0.037 mm) (50 g) was added and the mixture evaporated to dryness. The title product, N-(N-(6-chloro-3-pyridyl)-3-aminobutyl)phthalimide, was isolated from the dried mixture by flash chromatography on a silica column using silica gel, 230 to 400 US mesh (0.062 mm to 0.037 mm), eluted with 5% methanol in dichloromethane in a yield of 2.2 g (35%) as a brown solid.

NMR (CDCl$_3$), delta: 1.6 (d, 3H), 2.2 (q, 2H), 3.8 (m, 2H), 4.05 (m, 1H), 7.45 (d, 1H), 7.55 (d/d, 1H), 7.7 (m,2H), 7.85 (m, 2H), 8.25 (d, 1H), 10.2 (broad t, 1H).

EXAMPLE 6

Preparation of 1-amino-3-[N-(6-chloro-3-pyridyl)amino]butane

The product of Example 5 (2.2 g, 0.0067 mol) was dissolved in methanol (100 ml) and hydrazine hydrate (0.34 g, 0.0068 mol) Was added. The resulting mixture was heated under reflux for 5 hours. The resulting mixture was cooled to ambient temperature (20° C.), a mixture of concentrated hydrochloric acid (50 ml) and water (50 ml) was added and the resulting mixture was heated under reflux for a further 5 hours. The resulting mixture was cooled to ambient temperature (20° C.) and water (100 ml) was added. Potassium hydroxide was added until the mixture was rendered basic and the mixture was extracted with ( chloroform (3×150 ml). The combined chloroform extracts were dried and the solvent removed to leave the product 1-amino-3-[N-(6-chloro-3-pyridyl)amino]butane as a yellow oil in a yield of 0.94 g (70.6%).

EXAMPLE 7

Preparation of 2-nitromethylene-1-(6-chloro-3-pyridyl)hexahydropyrimidine

A mixture of N-(6-chloro-3-pyridyl)-1,3-diaminopropane (6.0 g, 0.032 mol)(ex Example 2), 1,1-bis(methylthio)-2-nitroethene (5.34 g, 0.032 mol) and ethanol (100 ml) was heated under reflux for 24 hours. The resulting mixture was evaporated to leave a dark brown oil which was subjected to flash chromatography on a silica column using silica gel, 230 to 400 US mesh (0.062 mm to 0.037 mm), and with 2% w methanol in dichloromethane as eluent. The resulting product was recrystalized from ethanol to give 2-nitromethylene-1-(6-chloro-3-pyridyl)hexahydropyrimidine as a pale yellow solid (3.1 g, 38%), m.p. 202° C.

EXAMPLE 8

Preparation of 2-nitromethylene-1-(6-chloro-3-pyridyl)imidazolidine

A mixture of N-(6-chloro-3-pyridyl)-1,2-diaminoethane (0.7 g, 0.0041 mol)(ex Example 4), 1,1-bis(methylthio)-2-nitroethene (0.7 g, 0.0042 mol) and ethanol (25 ml) was heated under reflux for 24 hours. The resulting mixture was evaporated to leave a dark brown oil which was subjected to flash chromatography on a silica column using silica gel, 230 to 400 US mesh (0.062 mm to 0.037 mm), and with 2% w methanol in dichloromethane as eluent. The resulting product was recrystalized from ethanol to give 2-nitromethylene-1-(6-chloro-3-pyridyl)imidazolidine as a pale yellow solid (0.225 g, 25%), m.p. 201° C.

EXAMPLES 9 AND 10

The following additional compounds were prepared by similar processes to those employed for the compounds of Examples 7 and 8:

9: 2-nitromethylene-1-(6-methoxy-3-pyridyl)hexahydropyrimidine (76%), m.p. 194° C.

NMR (CDCl$_3$), delta: 3.9 (s, 1H), 3.9 (m, 4H), 6.2 (s, 1H), 6.78 (d, 1H), 7.45 (d/d, 1H), 8.05 (d, 1H), 8.82 (broad s, 1H).

10: 2-nitromethylene-1-(6-methoxy-3-pyridyl)imidazolidine (66%), m.p. 194° C.

NMR (CDCl$_3$), delta: 2.2 (m, 2H), 3.6 (m, 4H), 3.93 (s, 3H), 6.0 (s, 1H), 6.79 (d, 1H), 7.4 (d/d, 1H), 8.0 (s, 1H), 10.85 (broad s, 1H).

EXAMPLES 11 AND 12

The following additional compounds were prepared by similar processes to those employed for the compounds of Examples 7 and 8:

11: 2-nitromethylene-1-(6-methylthio-3-pyridyl)hexahydropyrimidine (49%), m.p. 171° C.

NMR (CDCl$_3$), delta: 2.2(m,2H), 2.55(s,3H), 3.6(m,4H), 6.0(s,1H), 7.2(d,1H), 7.35(d/d,1H), 8.3(d,1H), 10.8(s,1H).

12: 2-nitromethylene-1-(6-methylthio-3-pyridyl)imidazolidine, m.p. 210° C.

NMR (CDCl$_3$), delta: 2.58(s,3H), 4.0(m,4H), 6.32(s,1H), 7.23(d,1H), 7.4(d/d,1H), 8.35(d,1H), 8.9(s,1H)

EXAMPLES 13 AND 14

The following additional compounds were prepared by similar processes to those employed for the compounds of Examples 7 and 8:

13: 2-nitromethylene-1-(6-bromo-3-pyridyl)hexahydropyrimidine (36%), m.p. 201° C.

NMR (CDCl$_3$) delta: 2.25(m,2H), 3.62(m,4H), 5.95(s,1H), 7.45(d/d, 1H), 7.6(d,1H), 8.3(d,1H), 10.86(s,1H).

14: 2-nitromethylene-1-(6-bromo-3-pyridyl)imidazolidine (45%), m.p. 202° to 203° C.

NMR (CDCl$_3$) delta: 3.72(t,2H), 4.0(t,2H), 6.16(s,1H), 7.7(d,1H), 7.77(d/d,1H), 8.4(d,1H), 9.32(s,1H).

EXAMPLE 15

Preparation of 2-nitro-2-acetylmethylene-1-(6-chloro-3-pyridyl)hexahydropyrimidine The product of Example 5 (1 g, 0.004 mol) was added to acetic anhydride (20 ml) and the resulting mixture heated to 60° C. The resulting mixture was cooled and filtered to yield a solid which, upon recrystallization from methanol, gave the product 2-nitro-2-acetylmethylene-1-(6-chloro-3-pyridyl)hexahydropyrimidine in a yield of 0.68 g (58%), m.p. 201° C.

NMR (CDCl$_3$) delta: 1.87(m,2H), 2.2(s,3H), 3.35(t,2H), 3.65(t,2H), 7.05(d,1H), 7.75(d/d,1H), 8.55(d,1H), 12.0(s,1H).

EXAMPLE 16

Preparation of 2-nitromethylene-1-(6-chloro-3-pyridyl)-6-methylhexahydropyrimidine A mixture of 1-amino-3-[N-(6-chloro-3-pyridyl)amino]butane (0.94 g, 0.0047 mol) (ex Example 6), 1,1-bis(methylthio)-2-nitroethene (0.78 g, 0.0047 mol) and ethanol (100 ml) was heated under reflux for 24 hours. The resulting mixture was cooled to ambient temperature (20° C.) and filtered to isolate the product 2-nitromethylene-1-(6-chloro-3-pyridyl)-6methylhexahydropyrimidine as a white solid in a yield of 0.3 g (25%), m.p. 184.5° C.

NMR (CDCl$_3$), delta: 1.23(d,3H), 2.0(m,1H), 2.3(m,1H), 3.6(m,2H), 3.83(m,1H), 5,85(s,1H), 7.43(d,1H), 7.75(d/d,1H), 8.25(d,1H), 10.95(s,1H).

EXAMPLE 17

Pesticidal Activity

Pesticidal activity of compounds of the invention was assessed against various of the following pests:

*Spodoptera littoralis* (Egyptian cotton leafworm)
*Aedes aeqypti* (yellow fever mosquito)
*Musca domestica* (housefly)
*Aphis fabae* (black bean aphid)
*Acyrthosiphon pisum* (pea aphid)
*Megoura viciae* (vetch aphid)
*Phaedon cochleariae* (mustard beetle)
*Plutella xylostella* (diamond-back moth)
*Trialeurodes vaporariorum* (greenhouse whitefly)
*Nephotettix cincticeps* (green leaf hopper)
*Nilaparvata lugens* (brown rice plant hopper)

The test methods employed for each species appear below. In each test, unless otherwise stated, solutions or suspensions of test compound were made up over a range of concentrations in water (initially 0.1%w) containing 10%w acetone and 0.025%w "TRITON X-100" (trade mark) surface active agent (the condensation product of ethylene oxide with an alkyl phenol). These solutions were sprayed at a rate equivalent to 340 liters per hectare ($3.4 \times 10^{-5}$ m$^3$/m$^2$) onto Petri dishes containing either test species per se or diet onto which test species were subsequently introduced, as indicated. The tests were all conducted under normal insectary conditions (23° C.±2° C., fluctuating humidity and light).

Mortality assessments were made as indicated below, in terms of percentage mortality figures. In each test a $LC_{50}$ (the dosage of active material required to kill half of the test species) for the compound was calculated from the mortality figures and compared with the corresponding $LC_{50}$ for a standard insecticide, ethyl parathion, in the same test. The results are expressed as toxicity indices thus:

$$\text{toxicity index} = \frac{LC_{50} \text{ (parathion)}}{LC_{50} \text{ (test compound)}} \times 100$$

(i) *Spodoptera littoralis* (7 day)(Sl 7D)

Test solutions were sprayed as indicated above onto Petri dishes containing a nutritious diet for Egyptian cotton leafworm larvae. When the spray deposit had dried, each dish was infested with ten 2nd instar larvae. Mortality assessments were made 7 days after spraying.

(ii) *Spodoptera littoralis* (foliar)(Sl Fol)

Test solutions were sprayed as described above onto Petri dishes containing 9 cm discs of Chinese cabbage leaves on filter papers. After drying, each dish was infested with ten 2nd instar larvae. Mortality assessments were made 24 hours after infestation.

(iii) *Spodoptera littoralis* (ovicidal)(Sl OA)

Test solutions were sprayed as described above onto Petri dishes containing filter papers on which were 50 24 hours old eggs. After 6 days the numbers of hatched and unhatched eggs were counted and percentage mortality calculated.

(iv) *Aedes aegypti* (Aa)

Early 4th instar larvae were used. Test solutions were made up to 0.5 ppm of test compound (and progressive half-dilutions) in water containing 0.04%w "TRITON X-100" (trade mark); acetone was initially present to aid solution, but was allowed to evaporate off before introduction of larvae.

Ten early 4th instar larvae were placed in 100 ml of test solution, and after 48 hours, larval mortality was recorded.

(v) *Musca domestica* (Md)

Batches of ten 2 to 3 day old milk-fed adult female houseflies, anesthetized using carbon dioxide, were placed on filter papers inside Petri dishes. The dishes were sprayed with the test solutions as described above. The flies were retained in the Petri dishes and were fed with a dilute milk solution which was dripped down the side of the Petri dish and absorbed by the filter paper. Mortality was assessed after 24 hours.

(vi) *Aphis fabae* (Af)

Tests were carried out on adult black bean aphids (*Aphis fabae*). Pairs of broad bean leaves on filter paper in Petri dishes were sprayed side by side with uncounted quantities of aphids in small gauze-covered containers. After passing through the spray ten aphids were tipped onto the leaves and lids were placed on the Petri dishes. Mortality was assessed after 24 hours.

(vii) *Acyrthosiphon pisum* (Ap)

Tests were carried out on young adult pea aphids. Whole pea plants 6 days after germination were placed on filter papers in Petri dishes. Ten aphids were transferred to each pea plant and left for 30 minutes to allow the aphids to settle and start to feed. The dishes were then sprayed with the test solutions as described above and lids were placed on the Petri dishes. Mortality was assessed after 24 hours.

(viii) *Megoura viciae* (Mv)

Tests were carried out on adult Vetch aphids in the same way as for black bean aphids in (vi) above.

(ix) *Phaedon cochleariae* (Pc)

Test solutions were sprayed as described above onto Petri dishes containing 9 cm discs of Chinese cabbage leaves on filter papers. After drying, each dish was infested with ten adult mustard beetles (up to 1 week old). Mortality assessments were made 24 hours after infestation.

(x) *Plutella xylostella* (Px)

Test solutions were sprayed as described above onto Petri dishes containing 9 cm discs of Chinese cabbage leaves on filter papers. After drying, each dish was infested with ten 3rd instar diamond-back moth larvae. Mortality assessments were made 24 hours after infestation.

(xi) *Trialeurodes vaporariorum* (Tv)

French bean plants (*Phaseolus vulgaris*) with two fully expanded leaves were placed in a breeding culture of *T. vaporariorum*, also on French bean plants, which were then disturbed to ensure resettlement on the introduced plants. During the subsequent 24 hour period, eggs were deposited and kept at 27° C., with 14 hours photoperiod. All adult whiteflies were then carefully removed, leaving egg samples of a known age. After eight days the majority of eggs had hatched. Leaf discs containing the newly hatched nymphs were then cut from the leaves and transferred to moist filter paper. The discs were examined under a low-powered microscope to determine the exact number of 1st instar nymphs per disc and to remove any unhatched eggs. On average, 70–100 nymphs were found per disc.

The discs were transferred into Petri dishes and sprayed with test solutions as described above. After 6 days percentage mortalities were assessed.

(xii) *Nephotettix cincticeps* (Nc)

Tests were carried out on young adult female green leaf hoppers. Plant pots, each containing five rice seedlings 10 to 15 cm tall arranged across the centre of the pot, were sprayed with test solutions as described above (but initial test concentration 0.05% of test compound). Spraying was on both sides of the plants with the pots horizontal. One hour after spraying, each pot was filled to the brim with fine silver sand, an open-ended glass jar was placed over each pot and each pot was infested with ten hoppers. A paper tissue was placed over the open end of each glass jar to retain the hoppers. The pots were irrigated from underneath, maintained at a temperature of 27° C.±2° C. and subjected to white fluorescent light under a regime of 18 hours light followed by 6 hours darkness. Mortality assessments were made 48 hours after infestation.

(xiii) *Nilaparvata lugens* (Nl)

Tests were carried out on young adult female brown rice plant hoppers in the same way as for green leaf hoppers in (xii) above.

Results of the above tests, only some of which were performed on each compound, are given in Table I following:

TABLE I

| Compound of Example | S17D | S1Fo1 | S1OA | Aa | Md | Af | Ap | Mv | Pc | Px | Tv | Nc | Nl |
|---|---|---|---|---|---|---|---|---|---|---|---|---|---|
| 7 | | | | | | 238 | 100 | 241 | 42 | 3 | 2550 | 3200 | 23000 |
| 8 | 27 | 48 | 77 | 3 | 9 | | 14 | 1520 | 205 | 23 | | 3700 | 7000 |
| 9 | | | 57 | 1 | | | 2 | | | | | 1140 | |
| 10 | 6 | 31 | | | | | 14 | | | | | 28 | |
| 11 | | | | | | | 3 | | | | | | 650 |
| 12 | | | | | | | 1 | | | | | | |
| 13 | | A | 290 | A | | | 18 | | | | | 5000 | 29680 |
| 14 | 8 | | 22 | 3 | | | 200 | | | | | 1240 | A |
| 15 | | | | | | | | | | | | 160 | 69 |
| 16 | | B | | | | | A | | | | | 2050 | |
| Comparative A | C | | C | C | C | | C | | | | | C | |

"Comparative A" is the compound 2-nitro-methylene-1-(4-chlorophenyl)imidazoline, m.p. 196° C., which was prepared in analogous manner to Example 6. Grade "C" under toxicity indices indicates that even at initial (i.e. highest) concentration of test compound less than 40% mortality of the pest was observed.

1. A nitromethylene compound of formula I $$R^1-N\overset{(CHR^2)_n}{\underset{\underset{R^3}{\overset{\|}{C}}\diagdown NO_2}{\diagup}}NH \quad (I)$$

wherein n is 2, 3 or 4;
$R^1$ is a 3-pyridyl group optionally substituted by one or more moieties selected from the group consisting of halogen, alkyl, alkoxy, alkylthio, haloalkyl, cyano, alkoxycarbonyl, alkylamino, dialkylamino, (alkylcarbonyl)alkylamino, (alkoxycarbonzyl)alkylamino, alkylcarbonylamino and alkoxycarbonylamino groups, in which any alkyl moiety contains from 1 to 6 carbon atoms;
each $R^2$ is independently at $C_{1-6}$ alkyl group, a $C_{1-6}$ haloalkyl group or a hydrogen atom; and
$R^3$ is a hydrogen atom or a ($C_{1-6}$ alkyl)carbonyl group.

2. A compound according to claim 1 wherein n is 2 or 3.

3. A compound according to claim 1 or 2 wherein $R^1$ is a 3-pyridyl group substituted in the 6-position by a halogen atom, a $C_{1-4}$ alkoxy group, a $C_{1-4}$ alkylthio group, a $C_{1-4}$ haloalkyl group, a cyano group or a ($C_{1-4}$ alkoxy)carbonyl group.

4. A compound according to claim 3 wherein $R^1$ is a 6-bromo-3-pyridyl group.

5. A compound according to claim 3 wherein $R^1$ is a 6-chloro-3-pyridyl group.

6. A pesticidal composition comprising a carrier and, as an active ingredient, an effective amount of a compound according to claim 1.

7. A method of combating pests at a locus which comprises treating the locus with an effective amount of a compound of formula I as claimed in claim 1.

* * * * *

UNITED STATES PATENT AND TRADEMARK OFFICE
CERTIFICATE OF CORRECTION

PATENT NO. : 5,039,686

DATED : August 13, 1991

INVENTOR(S) : JOHN H. DAVIES ET AL.

It is certified that error appears in the above-identified patent and that said Letters Patent is hereby corrected as shown below:

In the Abstract, at column 1, and in Claim 1 of the patent, formula (I) should read:

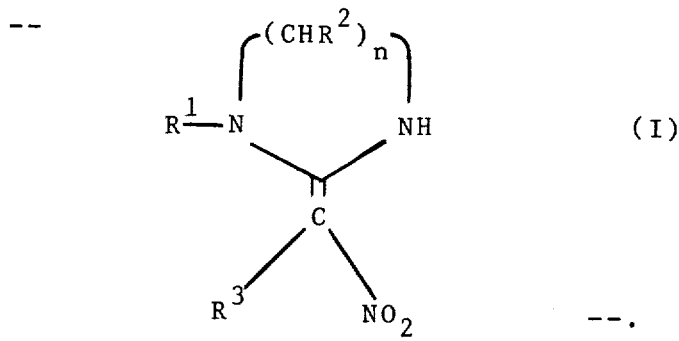

Column 13;

Claim 1, lines 11 and 12 of the claim, "(alkoxycarbonzyl)alkylamino" should read --(alkoxycarbonyl)alkylamino--.

Signed and Sealed this

Twelfth Day of January, 1993

Attest:

DOUGLAS B. COMER

Attesting Officer        Acting Commissioner of Patents and Trademarks